United States Patent [19]

Moteki et al.

[11] Patent Number: 5,078,943
[45] Date of Patent: Jan. 7, 1992

[54] PROCESS FOR MAKING SMALL DIAMETER STICKS

[75] Inventors: Tsutomu Moteki, Sodegauramachi; Kazuo Aoki, Chibashi; Kazuhiro Kimura, Ichiharashi, all of Japan

[73] Assignee: Chisso Corporation, Japan

[21] Appl. No.: 630,492

[22] Filed: Dec. 20, 1990

Related U.S. Application Data

[62] Division of Ser. No. 187,236, Apr. 28, 1988, Pat. No. 4,994,325.

[30] Foreign Application Priority Data

May 11, 1987 [JP] Japan .................. 62-113942

[51] Int. Cl.$^5$ .............................................. B29C 47/90
[52] U.S. Cl. .................. 264/209.5; 264/210.6; 264/210.7; 264/210.8; 264/211.14
[58] Field of Search ............ 264/210.7, 210.8, 210.4, 264/210.2, 210.3, 290.2, 178 F, 209.5, 210.6, 211.14; 425/379.1, 71

[56] References Cited

U.S. PATENT DOCUMENTS

| | | | |
|---|---|---|---|
| 2,842,790 | 7/1958 | Castelli | 604/1 X |
| 3,212,132 | 10/1965 | Westlake, Sr. | 425/379.1 |
| 3,255,494 | 6/1966 | Bloch et al. | 156/298 |
| 3,290,420 | 12/1966 | Orser | 264/210.2 |
| 3,367,926 | 2/1968 | Voeks | 264/331.17 X |
| 3,394,702 | 7/1968 | Heimlich et al. | 604/1 |
| 3,551,943 | 1/1971 | Staton et al. | 425/71 |
| 3,962,205 | 6/1976 | Ward et al. | 264/210.8 |
| 4,259,790 | 4/1981 | Borisof | 428/187 X |
| 4,287,149 | 9/1981 | Capaccio et al. | 264/210.8 |
| 4,339,499 | 7/1982 | Tappe | 264/210.7 |
| 4,384,098 | 5/1983 | Hagler et al. | 264/210.8 |
| 4,739,025 | 4/1988 | Burch | 264/210.8 |

FOREIGN PATENT DOCUMENTS

| | | | |
|---|---|---|---|
| 1017550 | 9/1977 | Canada | 264/210.4 |
| 59-191207 | 10/1984 | Japan | 264/290.2 |
| 61-234761 | 10/1986 | Japan . | |
| 933524 | 8/1963 | United Kingdom | 264/210.8 X |

*Primary Examiner*—Jeffery Thurlow
*Attorney, Agent, or Firm*—Leydig, Voit & Mayer

[57] ABSTRACT

A process for making sticks of small diameter being highly stiff, difficult to break or crack and usable as a cotton swab, straw, sunokos", etc. is provided, which includes extruding a polypropylene resin having a crystallinity of 0.945 or more and a melt flow rate of 0.2 to 20 g/10 minutes and satisfying a relation between melt flow rate and Q value of $y \geq 2x+8$ wherein y represents Q value and x represents melt flow rate and stretching this stick to 5 times or more the original length thereof.

7 Claims, No Drawings

PROCESS FOR MAKING SMALL DIAMETER STICKS

RELATED APPLICATIONS

This application is a divisional application of Ser. No. 07/187,236, filed Apr. 28, 1988 now U.S. Pat. No. 4,994,325.

BACKGROUND OF THE INVENTION

1. Field of the Invention

This invention relates to a stick of small diameter suitably usable as cotton swab, "sunoko" (a Japanese term which means a number of parallel sticks of small diameter connected with yarns), straw, "sunoko" for growing green laver, etc.

2. Description of the Related Art

As sticks of small diameter used for cotton swab, "sunoko" for growing green laver, etc., metal sticks of small diameter or bamboo "sunoko" have so far been mainly used, but in recent years, paper or plastic sticks of small diameter have come to be used for cotton swab and plastic sticks of small diameter have come to be used for a number of "sunoko"s, straw, etc. As the plastics therefor, polypropylene has been mainly used.

Since sticks of small diameter using conventional polypropylene have a low stiffness (low flexural modulus), such sticks have raised drawbacks that they bend easily and further break or crack when strongly bent.

SUMMARY OF THE INVENTION

The present inventors have made extensive research in order to overcome the above drawbacks of polypropylene resin sticks of small diameter. As a result, we have found that when a polypropylene resin having a specified crystallinity and melt flow rate and also having a specified relation between its Q value (which is a specific value representing the molecular weight distribution of resin) and the melt flow rate or a polypropylene resin further containing a substance having a nucleating effect (which will be hereinafter referred to as "nucleating agent") added to the above-mentioned polypropylene resin is used as the raw material resin for polypropylene resin sticks of small diameter, followed by stretching these resins to 5 times or more the original length, then the above-mentioned drawbacks can be overcome.

As apparent from the foregoing, the object of the present invention is to provide a stick of small diameter made of a polypropylene resin, which has a high stiffness and is difficultly cracked when bent or folded.

The present invention has the following constitutions: (1) a stick of small diameter which comprises a polypropylene resin as the raw material resin thereof having a crystallinity of 0.945 or more and a melt flow rate of 0.2 to 20 g/10 minutes and satisfying a relation between melt flow rate and Q value expressed by the formula of $y \geq 2x + 8$ wherein y represents Q value and x represents melt flow rate, which stick of small diameter is obtained by extruding said polypropylene resin into a stick and stretching this stick to 5 times or more the original length thereof; and (2) a stick of small diameter according to the above item (1), wherein said polypropylene resin further contains a substance having a nucleating effect.

DETAILED DESCRIPTION OF PREFERRED EMBODIMENTS

The polypropylene resin used as the raw material resin for the stick of small diameter of the present invention has a crystallinity of 0.945 or more. If a polypropylene resin having a crystallinity less than 0.945 is used, the resulting stick of small diameter obtained therefrom has insufficient stiffness. The crystallinity is a characteristic value expressing a crystallizability (stereoregularity), and in general the larger this value, the higher the stiffness. Conventional polypropylene resins have a crystallinity in the range of 0.85 to 0.92. The crystallinity may be measured according to an analytical method such as infrared spectrophotometry or nuclear magnetic resonance analysis. For example, in the case of measurement according to infrared spectrophotometry, a test piece of a suitable thickness e.g. 40 $\mu$ is prepared and when its absorbances at wavenumbers of 977 $cm^{-1}$ and 997 $cm^{-1}$ are measured, the ratio of the absorbances (997/977) corresponds to the crystallinity.

The polypropylene resin used in the present invention has a melt flow rate in the range of 0.2 to 20 g/10 minutes, preferably 0.4 to 15 g/10 minutes. If the melt flow rate is less than 0.2 g/10 minutes, the fluidity of the resulting molten resin is inferior, while if it exceeds 20 g/10 minutes, the fluidity of the resulting molten resin is so high that production of the objective stick is difficult.

The polypropylene resin used in the present invention should satisfy a relationship between the melt flow rate (x) and Q value (y), expressed by a formula of $Y \geq 2x + 8$. The Q value means a characteristic value expressing the molecular weight distribution of resin as described above and refers to the ratio ($M_W/M_N$) of the weight average molecular weight ($M_W$) of the resin to the number average molecular weight ($M_N$) thereof. The larger the Q value, the broader the molecular weight distribution. Conventional polypropylene resins have a Q value in the range of 3 to 7. If a polypropylene resin having a Q value satisfying a relation expressed by a formula of $y < 2x + 8$ is used, the resulting stick of small diameter obtained therefrom is undesirable in that it tends to break or crack when folded or to become brittle when annealed.

Herein the melt flow rate (x) refers to the quantity of molten resin extruded during 10 minutes when a load of 2.16 Kg is loaded on the resin at 230° C. and may be measured according to JIS K-6758, and the Q value (y) may be measured according to gel permeation chromatography (GPC).

To the polypropylene resin used in the present invention may be added a substance having a nucleating effect i.e. a nucleating agent. Such a nucleating agent has no particular limitation. Its examples are aluminum p-t-butylbenzoate, sodium salt of methylenebis(2,4-di-t-butylphenol) acid phosphate, sodium phosphoric acid bis(4-t-butylphenyl), dibenzylidene sorbitol compounds, ethylenebisstearamide, talc, and mixtures of two or more of the foregoing. Addition of the nucleating agent to polypropylene resin can enhance the stiffness of the resulting stick of small diameter using the polypropylene resin; hence this is preferred. The proportion of the nucleating agent added is suitably in the range of 0.5 to 10% by weight based on the total weight of the resulting polypropylene resin in the case of talc or the like, and in the range of 0.05 to 0.4% by weight based thereon in the case of the above-mentioned organic compounds other than talc or the like. It is known that addition of a nucleating agent to polypropylene resins enhances the stiffness of the resin, but sticks of small diameter obtained using a blend of the nucleating agent with conventional polypropylene resins having a Q value of 3 to 7 have an enhanced stiffness, but tend to break or crack when folded. Whereas when the nucleating agent is added to the polypropylene resin used in the present invention having a larger Q value, sticks of small diameter obtained from the resulting blend have a high stiffness and yet cause no break or crack.

The polypropylene resin used in the present invention has no particular limitations other than having a crystallinity of 0.945 or more and a melt flow rate of 0.2 to 20 g/10 minutes and further satisfies the relation between the melt flow rate (x) and Q value (y) expressed by the formula of $y \geq 2+8$. Examples of the resin are propylene homopolymer; copolymers of propylene with one or more kinds of o-olefins such as ethylene, butene-1, 4-methylpentene-1, hexene-1, octene-1, etc. containing 70% by weight of propylene component therein; modified polypropylene resins obtained by modifying the above polypropylene resins with an unsaturated carboxylic acid or its anhydride such as acrylic acid, maleic anhydride, etc.; and mixtures of one or more kinds of the foregoing. The polypropylene resin referred to herein includes those obtained by blending compounding agent(s) such as various stabilizers with propylene homopolymer, propylene copolymers or modified polypropylenes with an unsaturated carboxylic acid or its anhydride.

The polymers for such polypropylene resins may be produced for example according to the following process: (A) a reaction product of an organoaluminum compound such as diethylaluminum monochloride with an electron donor such as diisoamyl ether is reacted with $TiCl_4$, followed by further reacting the resulting solid product with an electron donor such as diisoamyl ether and an electron acceptor such as $TiCl_4$, combining the resulting solid product (I) with an organoaluminum compound such as diethylaluminum chloride and an aromatic carboxylic acid ester such as methyl p-toluate (II) in a molar ratio (II/I) of the aromatic carboxylic acid ester (II) to the solid product (I) of 0.1 to 10.0 to prepare a catalyst and continuously polymerizing propylene or propylene with the above illustrated α-olefin in the presence of the catalyst to produce propylene homopolymer or copolymer. The process may be carried out ① employing 3 or more polymerization vessels connected in series;
② feeding the total quantity of the catalyst used to the first polymerization vessel and successively and continuously transferring the catalyst together with the resulting reaction mixture to the second et seq polymerization vessels;
③ using hydrogen as a molecular weight modifier and adjusting the hydrogen concentrations in the respective polymerization vessels so as to be successively reduced; and
④ successively forming polypropylene on the catalyst in the respective polymerization vessels and discharging the polypropylene from the final polymerization vessel. (B) An example of conditions employed in the above-mentioned production process is as follows:
① employment of three polymerization vessels;
② polymerization temperatures: 72° C. in any of the polymerization vessels;
③ polymerization pressures: 6 $Kg/cm^2G$ in the first polymerization vessel (Re#1), 8 $Kg/cm^2G$ in the second (Re#2) and 10 $Kg/cm^2G$ in the third (Re#3); and
④ hydrogen concentrations (% by mol in the gas phase part) and characteristics of the resulting polymers are as follows:

|  |  | $H_2$ concentration | | | Characteristics of polypropylene | | |
|---|---|---|---|---|---|---|---|
|  |  | Re #1 | Re #2 | Re #3 | MFR | Q value | Crystallinity |
| Product of this invention | Ex.-1 | 5 | 1.2 | 0.6 | 0.5 | 11 | 0.955 |
|  | Ex.-2 | 15 | 1.9 | 0.7 | 1.0 | 13 | " |
|  | Ex.-3 | 20 | 2 | 0.3 | 5 | 22 | " |
|  | Ex.-4 | 25 | 3 | 0.1 | 10 | 29 | " |
| *1 | Ex.-5 | 5 | 1.2 | 0.6 | 0.5 | 10 | 0.915 |
| *2 | Ex.-6 | 0.45 | — | — | 0.5 | 6 | 0.918 |

*1: Product obtained by using a conventional Ziegler-Natta type catalyst; its crystallinity is low.
*2: Product obtained by using a conventional Ziegler-Natta type catalyst and according to a one-stage polymerization.

The stick of small diameter of the present invention may be obtained according to the following process: a polypropylene resin or a polypropylene resin having a nucleating agent added to the former polypropylene resin, each having a crystallinity of 0-.945 or more and a melt flow rate of 0.2 to 20 g/10 minutes and also satisfying a relation between the melt flow rate (x) and the Q value (y) of $y \geq 2x+8$ is used and the polypropylene resin is melt-kneaded at a melt-kneading temperature of 180° to 300° C., preferably 200° to 250° C. by means of an extruder, followed by continuously extruding the resulting resin through a die having a solid or hollow nozzle and immediately draft-stretching the resulting extruded molten stick to 5 times or more, preferably 8 times or more the original length, or cooling the extruded molten stick down to a temperature range above the heat distortion temperature of the raw material resin of the stick and below the melting point thereof, thereafter leading it to a draw die having a diameter at its exit smaller than that at its inlet and draw-stretching it therethrough. The above draft-stretching and the draw-stretching may also be combined.

Further, the stick of small diameter of the present invention may also be obtained according to the following process: the above extruded molten stick is subjected to the above draft-stretching, followed successively by adjusting the temperature range to that above the heat distortion temperature of the raw material resin of the stick and below the melting temperature thereof, and continuously draw-stretching the resulting stick, i.e. a process of continuously carrying out draft-stretching and draw-stretching.

The above draw-stretching more raises the stiffness of the resulting stick of small diameter; hence the stretching is preferred.

If sticks of small diameter obtained by using polypropylene resins other than that defined in the present invention are subjected to draw-stretching in a temperature range above the heat distortion temperature of the raw material polypropylene resins thereof and below the melting point thereof, then the resulting sticks of small diameter are liable to break or crack, whereas the stick of small diameter of the present invention is difficult to break or crack even when they are stretched in a temperature range above heat distortion temperature and below the melting point.

Further, when the stick of small diameter of the present invention is annealed in a temperature range of 50° C. or higher and a temperature lower by 5° C. than the heat distortion temperature of the raw material polypropylene resin, for 5 hours or longer, its stiffness is improved and it is more difficult to break; hence such an annealing is preferred. If the annealing temperature is lower than 50° C., the annealing effect is small, while if it exceeds the temperature lower by 5° C. than the heat distortion temperature, the resulting stick of small diameter bends or the orientation imparted by the stretching is reduced to lower the stiffness of the stick and hence to be liable to break.

To the polypropylene resin of the present invention may be added a suitable additive component such as stabilizer, luster-improving agent, antistatic agent or UV absorber and besides, coloring agent, fire retardant, thermoplastic resins other than polypropylene resin and synthetic rubbers or inorganic fillers, in a range wherein the object of the present invention is not damaged.

The present invention will be described in more detail by way of Examples and Comparative examples, but it should not be construed to be limited thereto.

In addition, the testing methods employed in Examples and Comparative examples were carried out according to the following methods:
(1) Melt flow rate: according to JIS K-6758;
(2) Q value: according to gel permeation chromatography (GPC);
(3) Crystallinity: according to infrared spectrophotometry;
(4) Heat distortion temperature: according to JIS K-7207 (under a load of 4.6 Kgf/cm$^2$);
(5) Stiffness (flexibility);

When one end of a portion of about 100 mm long cut off from a stick is fixed onto a horizontal pedestal support and a load of 100 g is applied to the other end of the cut-off at a position (a supporting point) apart by 50 mm from the end of the pedestal support, the quantity of the cut-off bent is measured (unit: mm); and
(6) Break test:

When an Izod tester according to JIS K-6758 is employed; the clearance between the tip end of its hammer and the tip end of a support having a sample fixed thereonto is set to 15 mm; a stick is fixed onto the support; and an impact (20 Kg-cm) is applied to the sample, tests on whether or not the stick is broken at that time are carried out with 10 sticks to examine the percentage break.

EXAMPLES 1 TO 16 AND COMPARATIVE EXAMPLES 1 TO 10

Polypropylene resins each having a heat distortion temperature of 115° C. and a melting point (according to DSC method) of 165° C. and a melt flow rate (MFR), a crystallinity and a Q value each indicated in Table 1 shown later (Examples 1-12 and Comparative examples 1-5) or polypropylene resins further having a nucleating agent added to the former polypropylene resins having various physical properties as above (Examples 13-16 and Comparative examples 6-7) were respectively melt-extruded by means of an extruder having a bore diameter of 40 mm and provided with a hollow die at a melt-kneading temperature of 200° C., followed by subjecting the extruded molten stick to draft-stretching at a rate of 30 to 50 m/min. while passing it through a cooling water vessel to cool it, whereby sticks of small diameter having various stretching ratios indicated in Table 1 were obtained.

Sticks of small diameter obtained in Examples 4, 5, 10 and 15 and Comparative examples 3, 7 and 10 were each heated to a temperature of 120° to 160° C. and subjected to draw-stretching passing through a tapered draw die in stretching ratios indicated in Table 1. The sticks of small diameter obtained in these Examples and Comparative examples had an outer diameter of 2.5 mm and an internal diameter of 0.8 mm. Sticks of small diameter obtained in Examples and Comparative examples were subjected to measurements of bend quantity and percentage of breaks. The results are collectively shown in Table 1.

In addition, in the case of Comparative example 1, the fluidity of the molten resin was inferior so that molding into stick form was impossible, while in the case of Comparative example 8, the flow of the molten resin was too good so that molding into stick was also impossible.

As apparent from Table 1, the sticks of small diameter of the present invention obtained in the respective Examples had a small bend quantity i.e. a high stiffness so that they are difficult to break, whereas the sticks of small diameter obtained in Comparative examples 4 to 7 wherein polypropylene resins each had a crystallinity of 0.915 had a large bent quantity and a very high percentage breakage.

Further, sticks of small diameter obtained in Comparative examples 2 to 4 wherein polypropylene resins each having a relation between Q value (y) and melt flow rate (x) of $y < 2x + 8$, each had a large bent quantity and also a high percentage breakage. Still further, sticks of small diameter obtained in Comparative examples 9 and 10 wherein the crystallinity and Q value satisfy the relation of $y \geq 2x + 8$, but the stretching ratios are less than 5 times, each had a large bent quantity and also a high percentage break.

TABLE 1

| | Example | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| Characteristics of raw materials | | | | | | | | | | | | | |
| MFR (g/10 min.) | 0.5 | 0.5 | 0.5 | 0.5 | 0.5 | 0.5 | 0.5 | 0.5 | 2 | 2 | 6 | 15 | 2 |
| Crystallinity | 0.947 | 0.955 | 0.955 | 0.955 | 0.955 | 0.960 | 0.955 | 0.955 | 0.955 | 0.955 | 0.955 | 0.955 | 0.955 |
| Q value | 12 | 12 | 12 | 12 | 12 | 12 | 15 | 20 | 15 | 15 | 28 | 44 | 15 |
| Nucleating*[1] agent-1 (wt. %) | | | | | | | | | | | | | 0.1 |
| Nucleating*[2] agent-2 (wt. %) | | | | | | | | | | | | | |

TABLE 1-continued

| Stretching ratio | | | | | | | | | | | | | |
|---|---|---|---|---|---|---|---|---|---|---|---|---|---|
| Draft-stretching (times) | 8 | 8 | 12 | 3 | 3 | 12 | 8 | 8 | 8 | 3 | 8 | 8 | 8 |
| Draw stretching (times) | | | | 5 | 8 | | | | | 5 | | | |
| Physical properties | | | | | | | | | | | | | |
| Bent quantity (mm) | 12 | 11 | 10 | 9 | 8 | 9 | 10 | 9.5 | 10.5 | 8.5 | 11 | 11 | 10 |
| Percentage break (No. of broken sticks/No. of measured sticks) | 2/10 | 3/10 | 1/10 | 0/10 | 0/10 | 2/10 | 2/10 | 1/10 | 2/10 | 1/10 | 3/10 | 2/10 | 3/10 |

| | Example | | | Comparative example | | | | | | | | | |
|---|---|---|---|---|---|---|---|---|---|---|---|---|---|
| | 14 | 15 | 16 | 1 | 2 | 3 | 4 | 5 | 6 | 7 | 8 | 9 | 10 |
| Characteristics of raw materials | | | | | | | | | | | | | |
| MFR (g/10 min.) | 2 | 2 | 2 | 0.1 | 0.5 | 0.5 | 2 | 2 | 2 | 2 | 25 | 0.5 | 0.5 |
| Crystallinity | 0.955 | 0.955 | 0.955 | 0.955 | 0.955 | 0.955 | 0.915 | 0.915 | 0.915 | 0.915 | 0.955 | 0.955 | 0.955 |
| Q value | 15 | 15 | 15 | 12 | 5 | 5 | 15 | 6 | 15 | 15 | 60 | 12 | 12 |
| Nucleating*1 agent-1 (wt. %) | 0.2 | 0.2 | | | | | | | 0.2 | 0.2 | | | |
| Nucleating*2 agent-2 (wt. %) | | | 0.1 | | | | | | | | | | |
| Stretching ratio | | | | | | | | | | | | | |
| Draft-stretching (times) | 8 | 3 | 8 | | 8 | 3 | 8 | 8 | 8 | 3 | 8 | 3 | 2 |
| Draw-stretching (times) | | 5 | | | | 5 | | | | 5 | | | 2 |
| Physical properties | | | | | | | | | | | | | |
| Bent quantity (mm) | 9 | 7.5 | 8 | | 15 | 13 | 17 | 20 | 16 | 14 | | 15 | 14 |
| Percentage break (No. of broken sticks/No. of measured sticks) | 3/10 | 1/10 | 2/10 | | 9/10 | 7/10 | 5/10 | 8/10 | 10/10 | 8/10 | | 7/10 | 6/10 |

*1 aluminum p-t-butylbenzoate
*2 Na salt of methylenebis(2,4-di-t-butylphenol)acid phosphate The stick of small diameter of the present invention has a high stiffness and difficultly breaks and cracks only with difficulty; hence it is adequately usable as cotton swab, straw and "sunoko"s such as "sunoko" for growing green laver.

What we claim is:

1. A process for forming a thin stretched polypropylene stick comprising:
   extruding a polypropylene resin having a crystallinity of at least 0.945 and a melt flow rate (x) of 0.2 to 20g/10 minutes and satisfying the relationship between x and Q value expressed by the formula $y \geq 2x+8$ wherein Y represents the Q value;
   stretching the resulting extruded molten stick to a length at least 5 times its original length.

2. The process according to claim 1 wherein the extruded molten stick is draft-stretched.

3. The process according to claim 1 wherein the extruded molten stick is draw-stretched.

4. The process according to claim 1 wherein said extruded molten stick is cooled after extrusion.

5. The process according to claim 4 wherein said extruded molten stick is cooled to a temperature in a range above the heat distortion temperature of the polypropylene resin and below the melting temperature thereof.

6. The process according to claim 9 wherein the extruded molten stick is both draft-stretched and draw-stretched.

7. The process according to claim 1 wherein the polypropylene resin is melt-kneaded prior to extrusion.

* * * * *

UNITED STATES PATENT AND TRADEMARK OFFICE
CERTIFICATE OF CORRECTION

PATENT NO. : 5,078,943

DATED : January 7, 1992

INVENTOR(S) : Moteki et al.

It is certified that error appears in the above-identified patent and that said Letters Patent is hereby corrected as shown below:

On the title page:
Item No. [54], Title, before "Process" insert --A--.

Claim 1, column 7, line 51, change "20g/10" to --20 g/10--;

line 53, change "Y" to --y--.

Claim 6, column 8, line 50, change "9" to --1--.

Signed and Sealed this

Twenty-second Day of June, 1993

Attest:

MICHAEL K. KIRK

*Attesting Officer*     Acting Commissioner of Patents and Trademarks